United States Patent [19]

Babkow

[11] Patent Number: 5,174,278
[45] Date of Patent: Dec. 29, 1992

[54] DOWNWARD ROTATING SPECULUM WITH CONICAL SHAPED BLADES

[76] Inventor: Beth Babkow, 7770 Youngdale Way, #E, Stanton, Calif. 90680

[21] Appl. No.: 618,068

[22] Filed: Nov. 26, 1990

[51] Int. Cl.⁵ .............................................. A61B 1/32
[52] U.S. Cl. ........................................ 128/17; 128/20
[58] Field of Search ................... 128/3, 12, 15, 17-20

[56] References Cited

U.S. PATENT DOCUMENTS

| | | | |
|---|---|---|---|
| 1,613,373 | 1/1927 | Beck | 128/15 |
| 2,544,932 | 3/1951 | Marco | 128/17 |
| 2,661,735 | 12/1953 | Davis | 128/17 |
| 2,809,628 | 10/1957 | Jonas | 128/17 |
| 3,332,414 | 7/1967 | Gasper | 128/17 |
| 3,565,061 | 2/1971 | Reynolds | 128/20 |
| 3,734,084 | 5/1973 | Ousterhout | 128/15 |
| 4,052,980 | 10/1977 | Grams et al. | 128/18 |
| 4,385,626 | 5/1983 | Danz | 128/17 |
| 4,597,383 | 7/1986 | Van Der Bel | 128/18 |
| 4,766,887 | 8/1988 | Cecil, Jr. et al. | 128/17 |

FOREIGN PATENT DOCUMENTS 2610507  8/1988  France ............................ 128/17

Primary Examiner—Stephen C. Pellegrino
Assistant Examiner—Ralph A. Lewis
Attorney, Agent, or Firm—Beech & Collins

[57] ABSTRACT

The improved speculum has a downward rotating lower blade, an upward handle, upper and lower blades thicker at the base and narrower at the insertion end with blade surfaces recessed to allow tissue to be held in the recessed area and with transverse recessions that allow the tissue to grip the device.

7 Claims, 2 Drawing Sheets

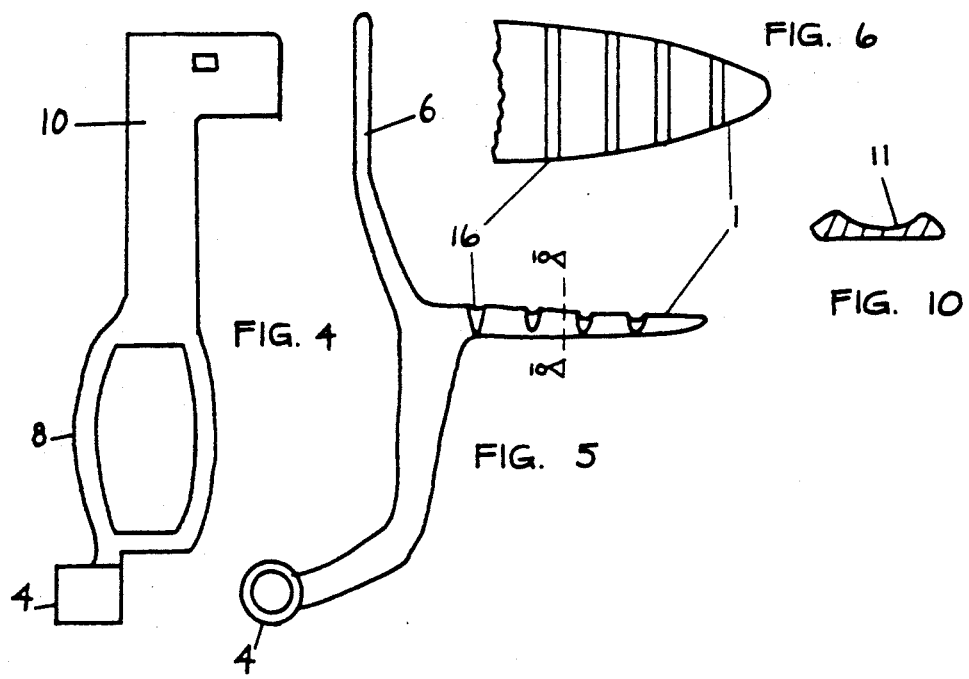
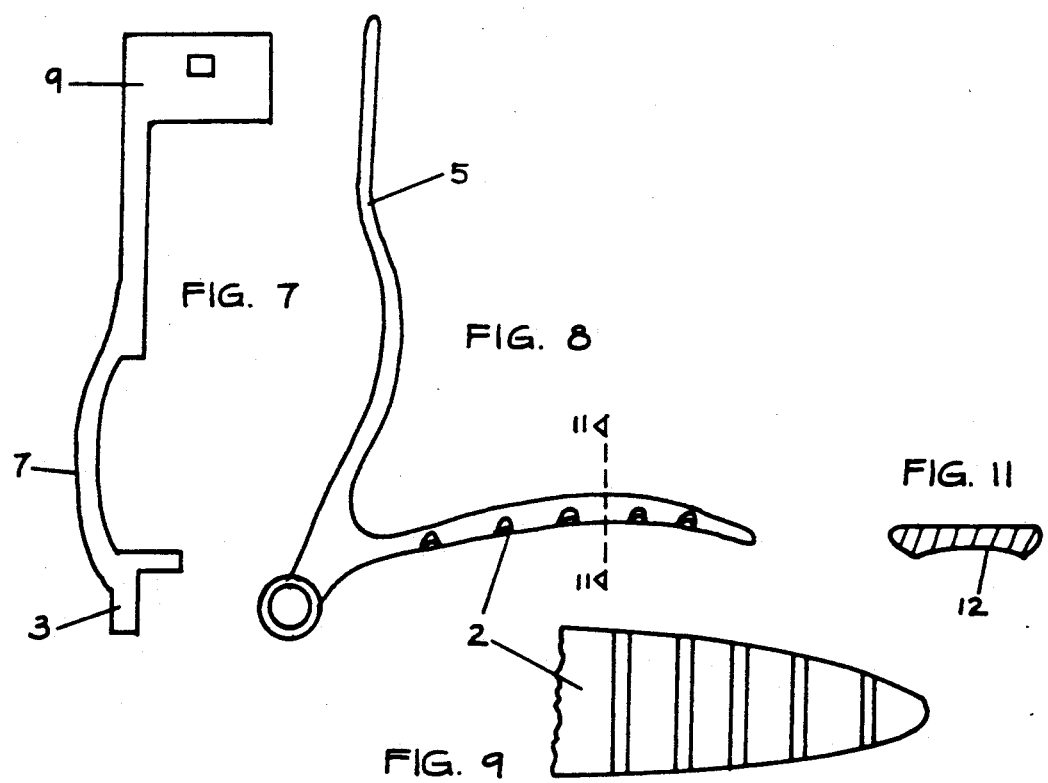

DOWNWARD ROTATING SPECULUM WITH CONICAL SHAPED BLADES

FIELD OF THE INVENTION

The downward rotating speculum is an improved speculum and pertains to those devices used to expand the opening of a body cavity.

DESCRIPTION OF RELATED ART

Currently available speculum, especially for vaginal examination, are closed, inserted sideways, rotated ninety (90) degrees and then the blades are spread. The general configuration of the device has the blades widening at the open end of the blade and are shaped in a smooth circular manner. These devices tend to rotate the upper blade surface. When the blades are spread pressure is extended on the inflexible areas of the body, such as the pubic bone, and stretches the constricted vaginal opening. The procedure causes discomfort. Current devices also allow tissue bloated by fatty tissue that is being forced apart to move around the speculum and enter the space created as the blades are separated. The entry of the tissue is especially a problem when examining overweight or individuals with high incident of fatty tissue in the vaginal area. Current devices also rely on the greater area of the open end of the speculum to keep the device firm during examination, further increasing the tendency to cause a level of discomfort.

The instant invention overcomes these disadvantages by having a narrow opening at the end allowing easy insertion. The lower blade expands into non-sensitive soft tissue reducing the discomfort. The entire upper blade serves as a static surface distributing the required force needed for separation of the tissue. The distribution of the forces along the upper blade reduces the force on the more sensitive tissue around the pubic bone. Recesses are located transverse to the blade length to allow the vaginal constrictions to hold the blades from slipping out and the surface of the upper and lower blades' outer surface are curved inward to hold the fatty tissue preventing if from entering the opening area. The examiner is better able to perform an examination as the area of interest is less obstructed.

SUMMARY OF THE INVENTION

The object of the downward rotating speculum is to provide a speculum for use in examinations such as those required for vaginal medical examination that provides a more comfortable device for such examination. Other objectives include providing a more visible examination area of the difficult patient. The device is intended to increase pressure on the less sensitive tissue proximal to the cervix and providing an inwardly curved surface. Other objectives will become apparent when the specifications and drawings submitted herein are reviewed.

BRIEF DESCRIPTION OF THE DRAWINGS

FIG. 4 is an end view of the upper blade.

FIG. 5 is a side view of the upper blade.

FIG. 6 is a top view of the upper blade.

FIG. 7 is an end view of the lower blade.

FIG. 8 is a side view of the lower blade.

FIG. 9 is a bottom view of the lower blade.

FIG. 10 is a cross-section of the upper blade.

FIG. 11 is a cross-section of the lower blade.

DESCRIPTION OF THE PREFERRED EMBODIMENT

Figure 1:
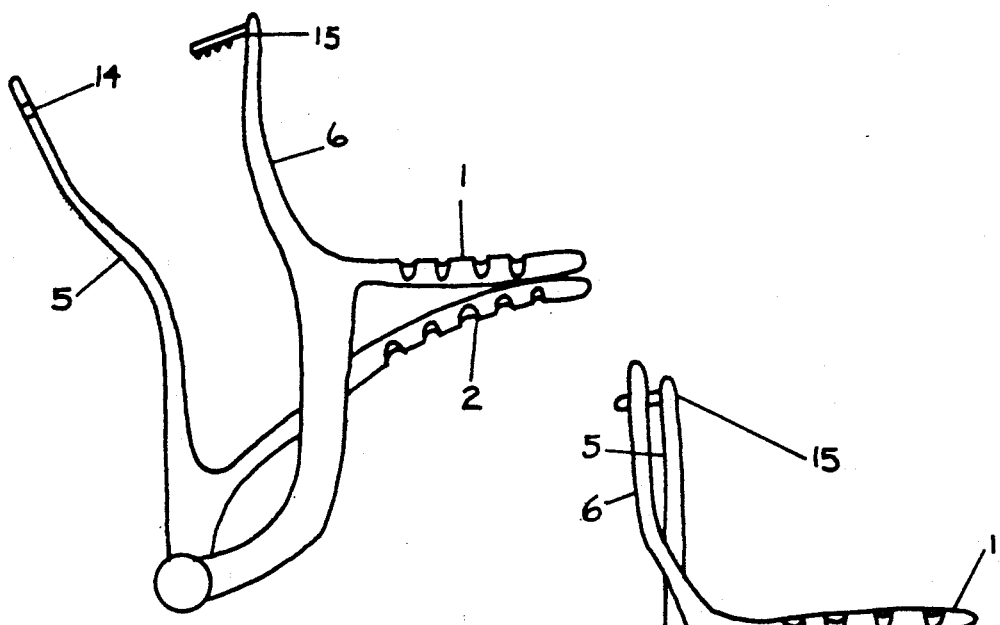
FIG. 1 is a side view of the device when the device is closed.
Figure 2:
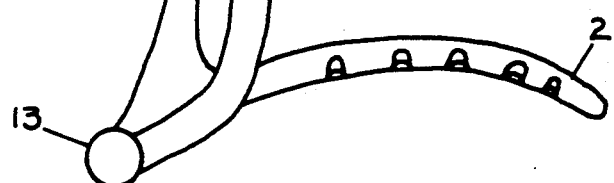
FIG. 2 is a side view of the device when the device is open.
Figure 3:
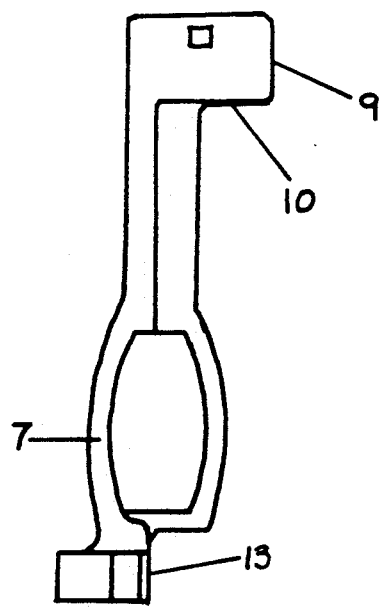
FIG. 3 is an end view of the device when the device is closed.

Referring to FIG. 1 through FIG. 3 the downward rotating speculum is illustrated. The speculum is comprised of four basic pieces. The upper blade (1), the lower blade (2), a hinge pin (13) and a temporary locking mechanism (14, 15).

FIG. 1 illustrates the device when the upper blade (1) and lower blade (2) are joined together. In use when performing a vaginal examination, the device is inserted with the upper and lower blades (1, 2) closed. The upper blade handle (6) and lower blade handle (5) are then joined together. The blades (1, 2) separate parting the tissue in the vaginal area. Near the end of the handle (6) a locking mechanism (15) is shown that locks with a corresponding locking mechanism on the lower blade handle (5) locking mechanism (14). The upper blade (1) rotates about a hinge pin assembly comprising an upper blade pin hinge (4) and lower blade hinge (3), when pin (13) is inserted and the upper blade (1) and lower blade (2) assemblies are joined.

Referring to FIGS. 4, 5, 6, and 10 the upper blade (1) surface (11) is concave. The surface (11) is shaped to keep tissue from moving around the sides of the device. The concave feature is especially useful for individuals having substantial fatty tissue in the area to be examined. The blade (1) is tapered from the widest area closest to the handles (6) to a smooth tip. Circumferential depressions (16) are formed at right angles to the blade length to allow muscle tissue in the vagina to contract around the recessed surface and hold the device firmly in place.

The locking mechanism (15) may be any type of temporary locking device that is easily locked while using the device and can be released easily while locking sufficient to keep the blades from closing in use. On the upper blade (1) the upper blade handle (6) is formed with a hole (8) in the part of the handle below the blade (1). The sides of the blade handle (6) are as slender as possible while being sufficiently strong to assure safe use of the device. The empty area allows the examiner to view into the space formed when the upper and lower blades (1, 2) are opened. A surface at the base of the window forms a ledge where swabs or tools may be rested during the examination. A widened surface (9, 10) at the end of the handle away from the hinge point is widened to allow the examiner with a more convenient point to apply pressure while opening the device during examination.

FIGS. 7, 8, 9 and 11 illustrate the lower blade (2). The device is designed to allow the lower blade (2) to move downward allowing the tissue to be gently separated.

As in the upper blade transverse recessed areas are provided on the external or lower surface. As in the upper blade the lower surface (12) the lower blade (2) is shaped to keep tissue from moving around the sides of the device.

On the lower blade (2) the lower blade handle (5) is formed with a curved side (7) above the low blade hinge (3). In the preferred embodiment the device is slightly curved downward along the length of the blade. The widen portion is located near the lower blade handle (5) and the cross-section narrows towards the tip.

The device may be of any size depending on the size of opening to be examined and the specific use.

I claim:

1. An improved speculum that is used to form a cavity for examination comprising:
   a. An upper blade assembly that has an upper blade with an insertion end that is inserted into a cavity, the upper blade is wider at the base than at the insertion end and the width extends gradually to a tapered end and the blade is attached to a first handle, the first handle is at approximately right angles to the upper blade with one end of the first handle extending sufficiently away from the blade to provide sufficient leverage when used by the hand of the person using the improved speculum to pry the material being separated and the other end of the first handle extending a sufficient distance away from the upper blade attachment point to rotate about a hinge positioned sufficiently away so as not to obstruct the user from viewing along the lower surface of the upper blade and
   b. a lower blade assembly that has a lower blade assembly with an insertion end that is inserted into a cavity the lower blade is wider at the base than at the insertion end and extends gradually to a tapered end and the blade is attached to a second handle at approximately right angles with the end of the handle extending sufficiently away from the blade to provide sufficient leverage when used by the hand of the person using the improved speculum to pry material being separated and the other end of the second handle extending sufficient distance away from the lower blade attachment point to rotate about a corresponding hinge mechanism that joins with the upper blade hinge mechanism such that when the handles are separated the blades are brought closer together and when the handles are joined the blades are separated and the side of the second handle is shaped as to not obstruct the view of the user when looking between the upper and lower blades when separated and the lower blade is curved away from the upper blade in a manner to gently separate the tissue and have the tissue held laterally in place.

2. An improved speculum as in claim 1 wherein the upper blade has transverse recession formed into the upper surface.

3. An improved speculum as in claim 1 wherein the lower blade transverse recession formed into the lower surface.

4. An improved speculum as in claim 1 wherein the upper blade has an axial depression along its length on the upper surface.

5. An improved speculum as in claim 1 wherein the lower blade lower surface has an axial depression along the blade length.

6. An improved speculum as in claim 1 wherein the hinge mechanism is a pin joining the upper blade handle and the lower blade handle.

7. An improved speculum as in claim 1 further comprising a locking mechanism having a piece of flexible notched material that has separate pieces attached to the upper blade handle and lower blade handle that when joined lock the mechanism and are easily separated to unlock the assembly.

* * * * *